US012569171B2

(12) United States Patent
Suri et al.

(10) Patent No.: US 12,569,171 B2
(45) Date of Patent: Mar. 10, 2026

(54) ELECTROCHEMICAL SENSING SYSTEM

(71) Applicant: Glucovation, Inc., Carlsbad, CA (US)

(72) Inventors: Jeff T. Suri, Fallbrook, CA (US); Robert Boock, Carlsbad, CA (US)

(73) Assignee: Glucovation, Inc.

( * ) Notice: Subject to any disclaimer, the term of this patent is extended or adjusted under 35 U.S.C. 154(b) by 0 days.

(21) Appl. No.: 17/577,544

(22) Filed: Jan. 18, 2022

(65) Prior Publication Data

US 2022/0211301 A1 Jul. 7, 2022

Related U.S. Application Data

(62) Division of application No. 15/731,058, filed as application No. PCT/US2015/020115 on Mar. 12, 2015, now Pat. No. 11,259,724.

(60) Provisional application No. 61/951,665, filed on Mar. 12, 2014.

(51) Int. Cl.

| | |
|---|---|
| ***A61B 5/1468*** | (2006.01) |
| ***G01N 27/28*** | (2006.01) |
| ***G01N 27/327*** | (2006.01) |
| ***G01N 27/416*** | (2006.01) |

(52) U.S. Cl.

CPC ........... *A61B 5/1468* (2013.01); *G01N 27/28* (2013.01); *G01N 27/327* (2013.01); *G01N 27/3271* (2013.01); *G01N 27/416* (2013.01)

(58) Field of Classification Search

None

See application file for complete search history.

(56) References Cited

U.S. PATENT DOCUMENTS

| | | | |
|---|---|---|---|
| 3,462,353 | A | 8/1969 | Banks et al. |
| 5,160,418 | A | 11/1992 | Mullen |
| 7,799,912 | B2 | 9/2010 | Conoci et al. |
| 8,224,410 | B2 | 7/2012 | Hadvary et al. |
| 8,658,795 | B2 | 2/2014 | Gamsey et al. |
| 8,668,820 | B2 | 3/2014 | Miyazaki et al. |
| 8,888,972 | B2 | 11/2014 | Lee et al. |
| 2003/0236448 | A1 | 12/2003 | Lu et al. |

(Continued)

FOREIGN PATENT DOCUMENTS

| | | | |
|---|---|---|---|
| CA | 1141435 | A | 2/1983 |
| JP | H09264870 | A | 10/1997 |

OTHER PUBLICATIONS

Ghica et al., A glucose biosensor using methyl viologen redox mediator on carbon film electrodes, Science Direct, Analytica Chimica Acta 532 (2005) 145-151, Available online Dec. 24, 2004.

*Primary Examiner* — J. Christopher Ball

(74) *Attorney, Agent, or Firm* — Garrett H. Anderson

(57) ABSTRACT

In some embodiments, an electrochemical sensing system includes a working electrode and a reference electrode. At least a portion of the working electrode includes rhodium. An electrical circuit is electronically coupled to the working electrode and the reference electrode. The electrical circuit is configured to bias the working electrode at voltage of less than about 0.4 V which is sufficient to electrochemically decompose a target analyte, and to measure a current corresponding to the concentration of the target analyte. In some embodiments, a biosensing molecule can be disposed on the working electrode and is operative to catalytically decompose a non-electroactive target analyte to yield and an electroactive by-product. In some embodiment, the reference electrode can include rhodium and its oxides.

18 Claims, 10 Drawing Sheets

(56) References Cited

U.S. PATENT DOCUMENTS

| | | | |
|---|---|---|---|
| 2005/0187097 | A1 | 8/2005 | Huang |
| 2010/0030045 | A1 | 2/2010 | Gottlieb et al. |
| 2010/0076283 | A1 | 3/2010 | Simpson et al. |
| 2010/0219084 | A1 | 9/2010 | Blythe et al. |
| 2011/0048972 | A1 | 3/2011 | Moffat et al. |
| 2011/0184264 | A1 | 7/2011 | Galasso et al. |

400

Clean a Substrate — 402

Electroplate Rhodium on the Substrate to Form a Working Electrode — 404

Electronically Couple the Working Electrode with a Reference Electrode to Form the Electrochemical Sensing System — 406

500

Select a Substrate Material — 502

Coextrude Rhodium with the Substrate Material to Form a Working Electrode — 504

Electronically Couple the Working Electrode with a Reference Electrode to Form the Electrochemical Sensing System — 506

600

Clean a Substrate — 602

Physically Deposit Rhodium on the Substrate to Form the Working Electrode — 604

Electronically Couple the Working Electrode with a Reference Electrode to Form the Electrochemical Sensing System — 606

700

Clean a Substrate          ～ 702

Chemically Deposit Rhodium on the
Substrate to Form the Working
Electrode          ～ 704

Electronically Couple the Working
Electrode with a Reference Electrode
to Form the Electrochemical Sensing
System          ～ 706

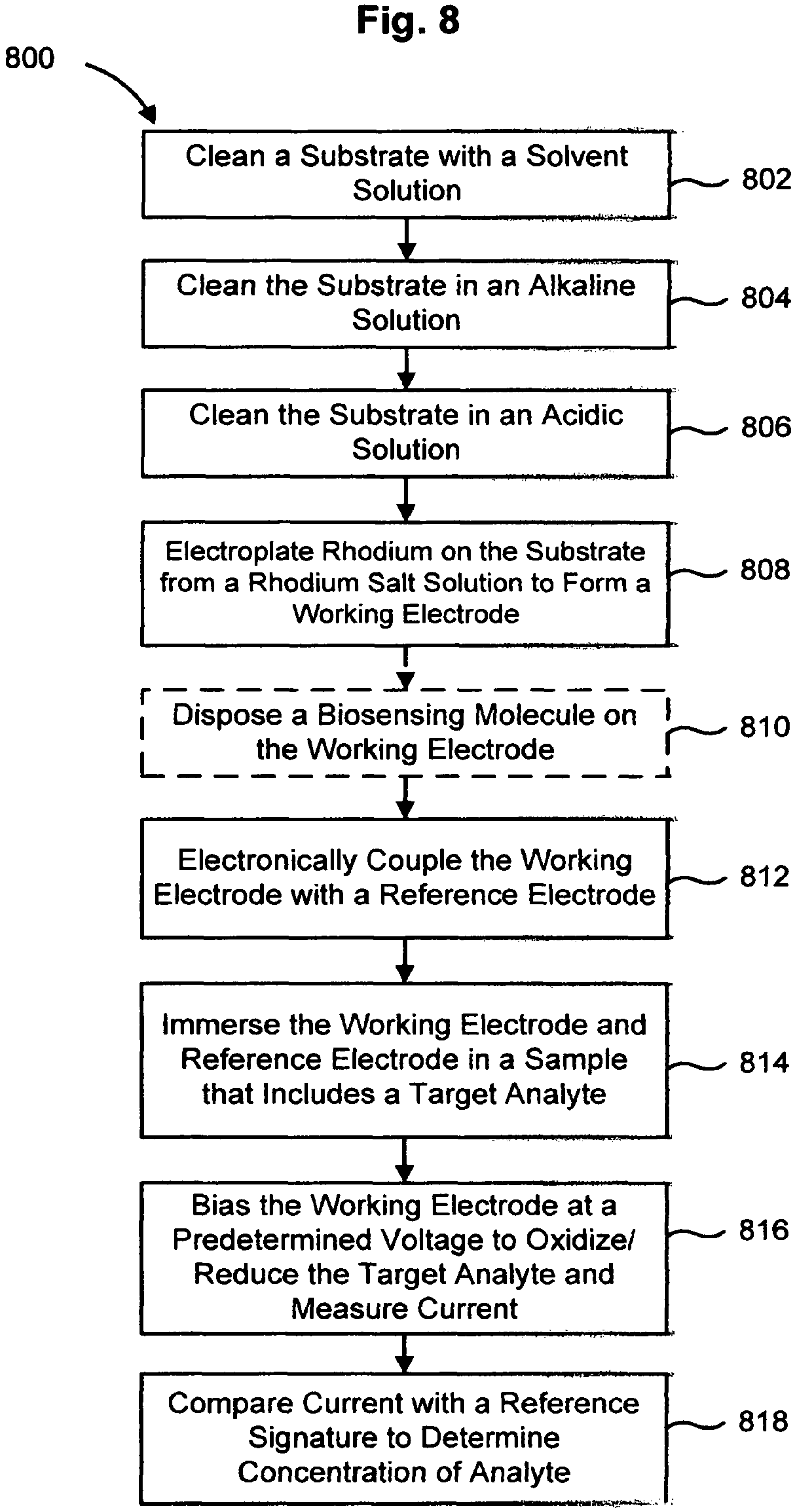

Clean a Substrate with a Solvent Solution — 802

↓

Clean the Substrate in an Alkaline Solution — 804

↓

Clean the Substrate in an Acidic Solution — 806

↓

Electroplate Rhodium on the Substrate from a Rhodium Salt Solution to Form a Working Electrode — 808

↓

Dispose a Biosensing Molecule on the Working Electrode — 810

↓

Electronically Couple the Working Electrode with a Reference Electrode — 812

↓

Immerse the Working Electrode and Reference Electrode in a Sample that Includes a Target Analyte — 814

↓

Bias the Working Electrode at a Predetermined Voltage to Oxidize/ Reduce the Target Analyte and Measure Current — 816

↓

Compare Current with a Reference Signature to Determine Concentration of Analyte — 818

ELECTROCHEMICAL SENSING SYSTEM

CROSS-REFERENCE TO RELATED APPLICATIONS

This application is a divisional of and claims benefit of priority to U.S. patent application Ser. No. 15/731,058 filed Apr. 12, 2017, to international patent application serial no. PCT/US2015/020115 filed 12 Mar. 2015 and to provisional patent application Ser. No. 61/951,665 filed Mar. 7, 2014, each entitled "Electrochemical Sensing System," the disclosures of which are hereby incorporated by reference in their entirety.

BACKGROUND

Embodiments described herein relate generally to electrochemical sensing systems that include a working electrode and a reference electrode, and in particular to electrochemical sensing systems that include a rhodium working electrode that can detect target analytes at a low bias voltage.

Electrochemical sensors are defined as sensors that employ an electronic parameter, for example, current, voltage, capacitance, impedance, or any other electronic parameter to measure the concentration of a target analyte, for example, a chemical or biochemical analyte. Among these electrochemical sensors, amperometric electrochemical sensors (i.e., current measuring sensors) are most popular. Amperometric electrochemical sensors can include a working electrode, a reference electrode and optionally, a ground electrode which is electronically coupled via an electrical circuit, for example, a potentiostat. The working electrode is biased at a predetermined positive (i.e., oxidation) or a predetermined negative (i.e., reduction) voltage, capable of oxidizing or reducing the target analyte, respectively. The redox reaction produces a current which is measured and compared with calibration plots to determine the concentration of the target analyte.

Known amperometric electrochemical sensors are also used as biosensors for sensing a non-electroactive target analyte, for example, a biomolecule such as glucose. Such known amperometric electrochemical sensors can include a biosensing molecule such as, for example, an enzyme or a synthetic biocatalyst immobilized on the surface of the working electrode. The biosensing molecule can catalytically decompose the non-electroactive biomolecule to yield an electroactive molecule and a by-product. For example, glucose oxidase decomposes glucose to yield gluconic acid, which is non-electroactive, and hydrogen peroxide which is electroactive. The electroactive hydrogen peroxide is oxidized or reduced on the surface of the working electrode to produce a current which is measured and is correlated to the concentration of the target analyte.

Known amperometric electrochemical sensors are often biased at a relatively high voltage, for example, a voltage of higher than about 0.5 V, to be able to oxidize or reduce the target analyte or its electroactive byproduct. At such high voltages, interfering electroactive chemical species that can also be present in a sample (e.g., a biological sample) that includes the target analyte can also get oxidized or reduced on the working electrode. This can significantly add to the noise and substantially reduce the signal to noise ratio of the electrochemical sensing system. For example, known enzymatic electrochemical sensors for measuring glucose in blood can include a working electrode biased at a voltage of 0.7 V, the optimum voltage for oxidizing hydrogen peroxide, which is the electroactive by-product of the enzymatic reaction. Blood however, can also include ascorbic acid, uric acid, and/or acetaminophen, which can all be oxidized at the 0.7 V voltage and contribute to the noise. Interferent blocking and/or repelling membranes can be used on the surface of the working electrode, however, they can reduce diffusion of the target analyte to the working electrode surface, thereby reducing the electrochemical signal. Known electrochemical systems also include working electrodes that use multi-step redox pathways (e.g., multiple enzymes, redox mediators, etc.) to facilitate electron transfer from or to the target analyte. This can allow biasing of the working electrode but can add to the complexity of the system, increase manufacturing costs, and reduce the signal amplitude.

Thus, it is an enduring goal of electrochemical sensing systems to develop new electrochemical sensors that have a higher signal to noise ratio, no baseline, and longer life.

SUMMARY

Embodiments described herein relate generally to electrochemical sensing systems that include a working electrode and a reference electrode, and in particular to electrochemical sensing systems that include a rhodium working electrode that can detect target analytes at a low bias voltage. In some embodiments, an electrochemical sensing system includes a working electrode and a reference electrode. At least a portion of the working electrode includes rhodium. An electrical circuit is electronically coupled to the working electrode and the reference electrode. The electrical circuit is configured to bias the working electrode at a voltage of less than about 0.4 V which is sufficient to electrochemically decompose a target analyte, and to measure a current corresponding to the concentration of the target analyte. In some embodiments, a biosensing molecule can be disposed on the working electrode and is operative to catalytically decompose a non-electroactive target analyte to yield an electroactive by-product. In some embodiment, the reference electrode can include rhodium and its oxides.

BRIEF DESCRIPTION OF THE DRAWINGS

FIG. 8 is a schematic flow diagram showing a method of forming an electrochemical sensing system and sensing a target analyte present in a sample using the electrochemical sensing system, according to an embodiment.

DETAILED DESCRIPTION

Figure 1:
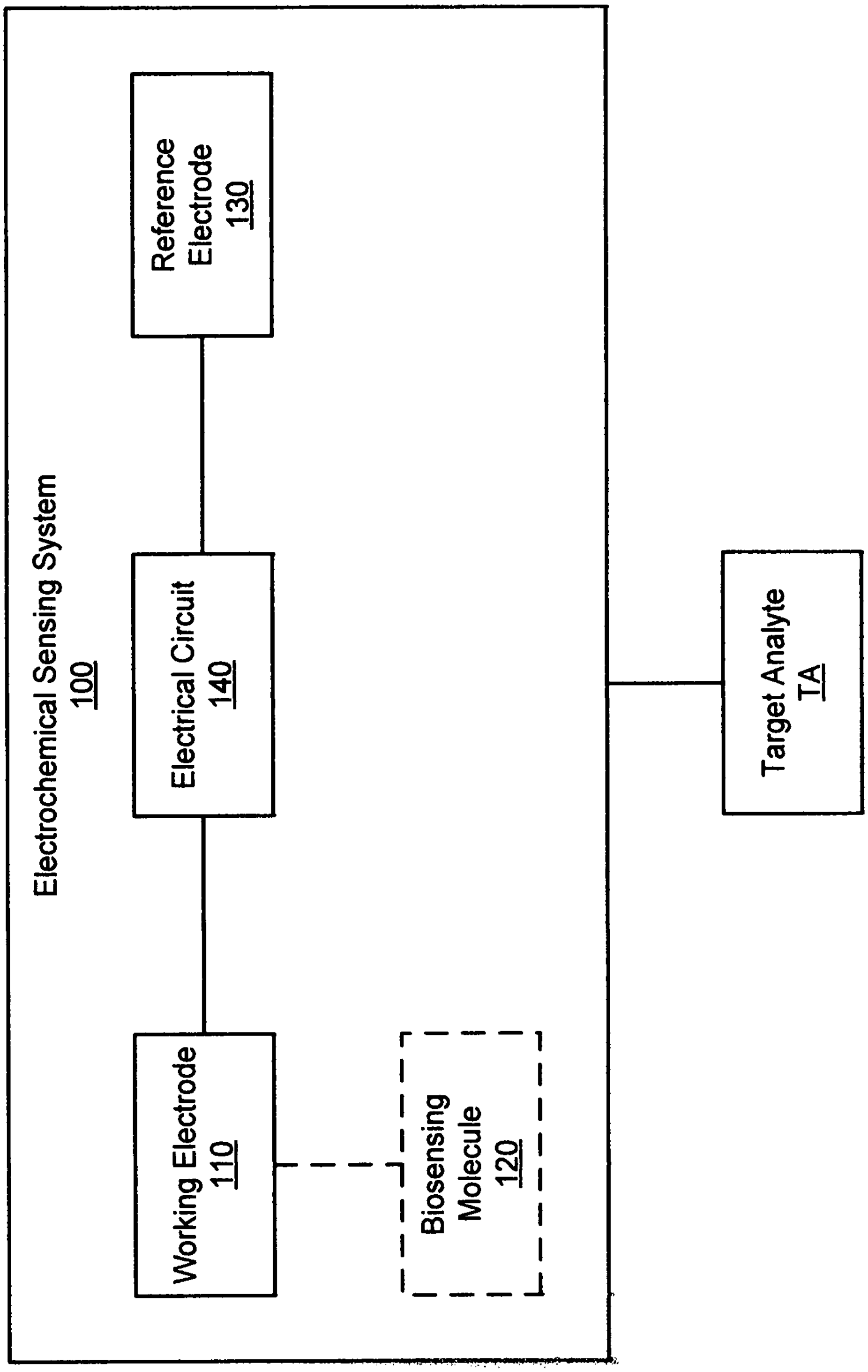
FIG. 1 is a schematic illustration of an electrochemical sensing system, according to an embodiment.

Conventional electrochemical systems often include working electrodes that are polarized at a relatively high bias voltage to oxidize or reduce a target analyte and produce a measurable current. Such high bias voltages can also oxidize or reduce interfering species, for example, interfering electroactive species present in a sample that includes the target analyte. This contributes to the "noise" (also referred to as interference) in the tested sample and can substantially decrease the signal to noise ratio.

Embodiments described herein relate generally to electrochemical sensing systems that include a working electrode and a reference electrode, and in particular to electrochemical sensing systems that include a rhodium working electrode which can detect target analytes at a low bias voltage. Embodiments of the electrochemical sensing system described herein offer several advantages over conventional electrochemical sensing systems including, for example: (1) providing a low biasing voltage operative to oxidize or reduce a target analyte or a by product of the target analyte, without oxidizing or reducing interfering species, thereby significantly increasing the signal to noise ratio and eliminating baseline; (2) configurable as a chemical sensor and/or a biosensor for sensing biochemicals; (3) configurable to detect a target analyte in vitro or in vivo (e.g., an in vivo glucose sensor disposed on the body of an animal or a human); (4) reduces fouling of the working electrode, thereby substantially increasing the sensitivity, repeatability, and lifetime of the electrochemical sensing system; and (5) providing repeatability of measurements which ensure that a single calibration can be used to correlate redox current to the concentration of the target analyte, over the lifetime of the electrochemical sensing system.

Embodiments described herein relate generally to electrochemical sensing systems that include a working electrode and a reference electrode, and in particular to electrochemical sensing systems that includes a rhodium working electrode that can detect target analytes at a low bias voltage. In some embodiments, an electrochemical sensing system includes a working electrode and a reference electrode. At least a portion of the working electrode includes rhodium. An electrical circuit is electronically coupled to the working electrode and the reference electrode. The electrical circuit is operable to: (a) bias the working electrode at a voltage of less than about 0.4 V such that a target analyte decomposes, and (b) measure a current corresponding to the concentration of the target analyte. In some embodiments, a biosensing molecule can be disposed on the working electrode and is operative to catalytically decompose a non-electroactive target analyte to yield an electroactive by-product. In some embodiments, the reference electrode can include rhodium and its oxides.

In some embodiments, an electrochemical sensing system includes a working electrode and a reference electrode. At least a portion of the reference electrode includes rhodium and its oxides. An electrical circuit is electronically coupled to the working electrode and the reference electrode. The electrical circuit is operable to: (a) bias the working electrode at a voltage of less than about 0.4 V such that a target analyte decomposes, and (b) measure a current corresponding to the concentration of the target analyte.

In some embodiments, an electrochemical sensing system includes a working electrode and a reference electrode. At least a portion of the reference electrode includes palladium and its oxides. An electrical circuit is electronically coupled to the working electrode and the reference electrode. The electrical circuit is operable to: (a) bias the working electrode at a voltage of less than about 0.4 V such that a target analyte decomposes, and (b) measure a current corresponding to the concentration of the target analyte.

In some embodiments, an electrochemical sensing system includes a working electrode and a reference electrode. At least a portion of the reference electrode includes irdium and its oxides. An electrical circuit is electronically coupled to the working electrode and the reference electrode. The electrical circuit is operable to: (a) bias the working electrode at a voltage of less than about 0.4 V such that a target analyte decomposes, and (b) measure a current corresponding to the concentration of the target analyte.

In some embodiments, an electrochemical sensing system includes a working electrode and a reference electrode. At least a portion of the working electrode includes rhodium. A synthetic redox-active receptor is disposed on the working electrode and is configured to move between different electronic states. The synthetic redox-active receptor changes its reduction potential as a result of reaction with a target analyte. An electrical circuit is electronically coupled to the working electrode and the reference electrode. The electrical circuit is operable to bias the working electrode at a voltage of less than about 0.4 V such that the working electrode accepts and/or donates an electron from or to the synthetic redox-active receptor and moves the synthetic redox-active receptor into a more oxidized or reduced state.

As used herein, the term "about" and "approximately" generally mean plus or minus 10% of the value stated, e.g., about 250 μm would include 225 μm to 275 μm, about 1,000 μm would include 900 μm to 1,100 μm.

As used herein, the term "target analyte" refers to a chemical or a biochemical that can be sensed by embodiments of the electrochemical sensing system described herein.

As used herein, the term "electroactive" means a chemical or a biochemical that can be electrochemically oxidized or reduced at an electrode biased at an appropriate biasing voltage.

As used herein, the term "interferents" refers to chemicals or biochemicals (except a target analyte) that are electroactive and can undergo a redox reaction at a working electrode included in any embodiments of the electrochemical sensing system described herein, and that contributes to noise.

As used herein, the term "baseline" refers to unpredictable noise that varies from sensor to sensor and is the intercept "b" term of the current vs. concentration plot (y=mx+b).

As used herein, the term "sensitivity" refers to the slope "m" term of the current vs. concentration plot (y=mx+b).

FIG. 1 shows a schematic illustration of an electrochemical sensing system 100, according to an embodiment. The electrochemical system 100 includes a working electrode 110, a reference electrode 130 and an electrical circuit 140. Optionally, a biosensing molecule 120 can be disposed on the working electrode 110. The electrochemical sensing system 100 can be configured to interact with a target analyte TA to electrochemically decompose (i.e., oxidize or reduce) the target analyte TA, and measure a redox current corresponding to the concentration of the target analyte TA.

The working electrode 110 can include a rhodium electrode, or an electrode having rhodium disposed thereon. The working electrode 110 can be configured to oxidize a target analyte TA at a biasing voltage of less than about 0.4 V such that oxidation and reduction of one or more interfering species on the working electrode 110 is substantially reduced. Without being bound by any particular theory, rhodium can catalytically oxidize or reduce the target analyte TA, such that a relatively low bias voltage, for example, less than about 0.4 V, is sufficient to oxidize or reduce the target analyte TA or an electroactive by-product of the target analyte TA. In some embodiments, the biasing voltage can be, less than about 0.35 V, less than about 0.3 V, less than about 0.25 V, less than about 0.20 V, less than about 0.15 V, less than about 0.1 V, less than about 0.05 V, or about 0 V, inclusive of all ranges therebetween. The bias voltage can be sufficiently low such that interferents (e.g., interfering electroactive species present in a sample that includes the target analyte TA) are not oxidized or reduced on the working electrode 110. In some embodiments, the working electrode 110 can be formed from an oxide of rhodium, for example $RhO_2$, $Rh(OH)_3$ or $Rh_2O_3$. In some embodiments, a blend of rhodium and another metal, for example, ruthenium, platinum, palladium, gold, nickel, any other suitable metal or alloy, can be used to form the working electrode 110.

In some embodiments, the working electrode 110 can be a pure rhodium electrode. In some embodiments, the working electrode 110 can include a substrate on which rhodium is disposed. The substrate can be formed from any suitable conductive material that has good adhesion with rhodium, for example, chromium, titanium, nitinol, gold, platinum, nickel, palladium, stainless steel, any other suitable material or combination thereof. The rhodium can be disposed on the substrate using any suitable process. For example, in some embodiments, the rhodium can be electroplated over the substrate. Any suitable rhodium salt solution can be used to electroplate rhodium on the substrate, for example, a rhodium sulfate solution, a rhodium chloride solution, any other rhodium plating solution or combination thereof. The deposition voltage and/or time can be controlled to obtain a predetermined thickness of rhodium on the substrate.

In some embodiments, the rhodium can be disposed on the substrate using a co-extrusion process, for example, when forming a cylindrical working electrode 110. In some embodiments, a physical deposition process can be used to dispose rhodium on the substrate. Such processes can include, for example, casting or a physical vapor deposition (PVD) process such as, for example, e-beam evaporation, thermal evaporation, sputtering, atomic layer deposition (ALD), pulsed laser deposition (PLD), any other physical vapor deposition process or a combination thereof. In some embodiments, a chemical vapor deposition (CVD) process can be used to dispose rhodium on the substrate. Suitable processes can include, for example, low pressure chemical vapor deposition (LPCVD), plasma enhanced chemical vapor deposition (PECVD), molecular beam epitaxy (MBE), any other suitable chemical vapor deposition process or combination thereof. In some embodiments, self assembly can be used to dispose rhodium on the substrate. For example, rhodium nanoparticles can be urged to self assemble on the substrate to form the working electrode 110. Use of a substrate formed from a material which has a high adhesion with rhodium and/or rhodium oxide can enable the deposition of the rhodium (or rhodium electrode) on any suitable substrate, for example, a plastic substrate (e.g., a high density polyethylene (HDPE) or a poly tetrafluoroethylene (PTFE)) substrate, a silicon substrate, or a TEFLON® substrate.

The working electrode 110 can have any suitable shape or size. For example, in some embodiments, the working electrode 110 can be a rod having a circular, oval, or polygonal cross-section. In such embodiments, the working electrode 110 can be a solid cylindrical electrode or a hollow cylindrical electrode (e.g., a cylindrical electrode that defines a lumen). In some embodiments, the working electrode 110 can be a needle type electrode which can, for example, be configured to be inserted into an animal or human body for measuring the concentration of the target analyte TA. In some embodiments, the working electrode 110 can be a flat electrode, for example, a flat plate, a disc, a solid state microfabricated electrode (e.g., of the type used in MEMS devices), or a screen printed electrode. In some embodiments, at least a portion of the working electrode 110 can be insulated with an insulating material, for example, rubber, TEFLON®, plastic, parylene, silicon dioxide, silicon nitride, any other suitable insulation material or combination thereof. The insulation material can, for example, be used to define an active area of the working electrode 110.

In some embodiments, the working electrode 110 can be subjected to a surface modification process to modify a surface area of the rhodium, for example, to provide a larger surface area for the target analyte TA to undergo the redox reaction at the working electrode 110. Such surface modification processes can include, for example, etching (e.g., etching in an acidic or basic solution), voltage cycling (e.g., cyclic voltammetry), electrodeposition of colloidal rhodium, and any other suitable surface modification process or combination thereof. In some embodiments, the rhodium metal can be oxidized to yield a rhodium oxide (e.g., rhodium dioxide) layer on the substrate. For example, the working electrode 110 can be immersed in an acidic bath, exposed to an oxygen plasma, any other suitable process or combination thereof can be used to oxidize the rhodium disposed on the substrate of the working electrode 110.

In some embodiments, a biosensing molecule 120 can optionally be disposed on the working electrode 110. In such embodiments, the target analyte TA can be a biomolecule which is non-electroactive. Such target analytes TA can include, for example, glucose, sucrose, glutamate, lactate, cholesterol, alcohol, aspartate transaminase, alkaline transaminase, alkaline phosphatase, urea, ascorbate, pyruvate, L-arginine, creatine, choline or any other biomolecule. The biosensing molecule 120 can be configured to catalytically decompose the non-electroactive target analyte TA and yield an electroactive by-product. The electroactive by-product can thereby, be oxidized or reduced at the working electrode 110 to yield a current which corresponds to the concentration of the target analyte TA. In some embodiments, the biosensing molecule 120 can be an enzyme such as, for example, glucose oxidase, glutamate oxidase, lactate oxidase, lactate dehydrogenase, cholesterol oxidase, ascorbate oxidase, pyruvate oxidase, myokinase, arginase, choline oxidase, creatine phosphokinase, phosphatase, any other suitable enzyme or combination thereof. For example, glucose oxidase can be disposed on the working electrode 110 for measuring the concentration of glucose (i.e., the target analyte) which is non-electroactive. The glucose oxidase enzymatically decomposes the glucose to yield gluconic acid and hydrogen peroxide. The hydrogen peroxide can be oxidized on the working electrode 110 at the low bias voltage of less than about 0.4 V (e.g., about 0.3 V) to produce a current, which can be correlated to the concentration of the glucose.

In some embodiments, a single biosensing molecule 120 can be used to decompose the non-electroactive target analyte TA to yield an electroactive by-product. In some embodiments, a series of biosensing molecules 120 can be disposed on the working electrode 110. For example, a first biosensing molecule can decompose the non-electroactive target analyte TA into intermediate non-electroactive by-products. A second biosensing molecule can then decompose at least one of the intermediate non-electroactive by-products to yield a final electroactive by-product. In some embodiments, a mediator or a transducer can be included with the biosensing molecule 120. The mediator or the transducer can serve as an intermediate electron carrier that can facilitate electron transfer to or from the working electrode 110, thereby reducing the bias voltage required to perform the redox reaction.

In some embodiments, the biosensing molecule 120 can be a synthetic redox-active receptor, for example, a viologen or a conjugated pyridinium. The synthetic redox-active receptor can be configured to be moved between different electronic states. For example, the synthetic redox-active receptor can bind or otherwise interact with the target analyte TA to change the synthetic receptor's reduction potential. The binding or otherwise interaction of the synthetic redox-active receptor with the target analyte TA can be an equilibrium reaction in which the target analyte TA does not decompose. The synthetic redox-active receptor can then communicate the accepted electron to the working electrode 110 and move into a different electronic state. This generates a current which can be measured by the electrical circuit 140, as described herein. In this manner a synthetic redox-active receptor can be used to electrochemically sense the target analyte TA, without the target analyte TA being consumed. Such synthetic redox-active receptors can have a higher stability than biomolecules. Thus, they can allow for better stability, lesser drift and longer lifetime of the working electrode 110.

The biosensing molecule 120 can be disposed on the surface of the working electrode 110 using any suitable means. In some embodiments, the biosensing molecule 120 can be physically adsorbed on the surface. In some embodiments, the biosensing molecule 120 can be covalently coupled to the surface of the rhodium on the working electrode 110, for example, using thiol chemistry. In some embodiments, the biosensing molecule 120 can be suspended in a porous membrane, for example, a polyurethane membrane, a silicone membrane, a glutaraldehyde membrane, a sol-gel membrane, a NAFION® membrane, any other suitable membrane or combination thereof, which is disposed on an outer surface of the working electrode 110.

In some embodiments, a selectivity layer (not shown) can be disposed on the working electrode 110, for example, disposed between the surface of the rhodium and the biosensing molecule 120. The selectivity layer can be configured to prevent electroactive interferents from coming in contact with the working electrode 110 and undergoing a redox reaction. For example, in some embodiments, the selectivity layer can be configured to repel oppositely charge ionic interferents. For example, a NAFION® selectivity layer can be disposed between an outer surface of the working electrode 110 and the biosensing molecule 120. The NAFION® is inherently negatively charged and repels negatively charged interferents such as, for example, ascorbic acid, but allows a neutral target analyte TA, such as hydrogen peroxide to diffuse through the NAFION® to the working electrode 110. In some embodiments, the selectivity layer can be a size exclusion layer, for example, a cellulose acetate layer. Such a selectivity layer can be porous and define a pore size such that only the small target analyte TA, for example, hydrogen peroxide can diffuse through the pores of the selectivity layer, while larger interferents such as, for example, ascorbic acid are blocked.

In some embodiments, a porous membrane (not shown) can be disposed over the biosensing molecule 120. The porous membrane can ensure substantially stable diffusion of the target analyte TA to the biosensing molecule 120 over the operational lifetime of the working electrode 110. Stable diffusion can ensure that any changes in the amperometric current measured by the electrochemical sensing system 100 is substantially due to a change in concentration of the target analyte TA and is not due to a variable flux of the target analyte TA to the biosensing molecule 120. In some embodiments, the porous membrane can be biocompatible. In some embodiments, the porous membrane can also prevent fouling of the working electrode 110, for example, biofouling due to proteins present in a biological sample. Examples of materials which can be used to form the porous membrane can include, for example, polyurethane, silicone, glutaraldehyde, a sol-gel, any other suitable diffusivity layer or combination thereof.

The reference electrode 130 is electronically coupled to the working electrode 110 via the electrical circuit 140. The reference electrode 130 can include any suitable reference electrode that can provide a stable reference voltage for the working electrode 110 and does not get consumed by the oxidation or reduction reaction, thereby providing longer shelf life, no usage limitations due to reference consumption, and substantially reduce signal drift. Suitable materials for the reference electrode 130 can include, for example, metal oxides (e.g., iridium oxide, ruthenium oxide, palladium oxide, platinum oxide, rhodium oxide), metal halides, conducting polymers (e.g., polyethylene dioxythiophene: polystyrene sulfonate (PEDOT:PSS), any other suitable stable reference electrode or combination thereof. In some embodiments, the reference electrode 130 can include rhodium and its oxides (e.g., $RhO_2$, $Rh(OH)_3$, $Rh_2O_3$, etc.). In some embodiments, the reference electrode 130 can include iridium and its oxides. In some embodiments, the reference electrode 130 can include palladium and its oxides.

The reference electrode 130 can have any shape or size. For example, in some embodiments, the reference electrode 130 can be a rod having a circular, oval, or polygonal cross-section. In some embodiments, the reference electrode 130 can be a needle type electrode which can, for example, be configured to be inserted into an animal or human body along with the working electrode 110. In some embodiments, the reference electrode 130 can be a flat electrode, for example, a flat plate, a disc, a solid state microfabricated electrode (e.g., of the type used in MEMS devices), or a screen printed electrode. In some embodiments, at least a portion of the reference electrode 130 can be insulated with an insulating material, for example, rubber, TEFLON®, plastic, parylene, silicon oxide, silicon nitride, any other suitable insulation material or combination thereof. The insulation material can, for example, be used to define an active area of the reference electrode 130. In some embodiments, the reference electrode 130 can have the same shape as the working electrode 110.

In some embodiments, a porous membrane (not shown) can be disposed over the surface of the reference electrode 130, for example, to prevent fouling of the reference electrode. For example, proteins in a biological solution (e.g., blood) in which the target analyte TA is being detected, can adhere to the surface of the reference electrode, thereby fouling the reference electrode 130, which can cause the formal voltage of the reference electrode 130 to drift. The porous membrane, for example, a biocompatible porous membrane can prevent the proteins from adhering to the reference electrode, thereby reducing fouling. Examples of materials which can be used to form the porous membrane can include, for example, polyurethane, glutaraldehyde, a sol-gel, any other suitable diffusivity layer or combination thereof.

As shown in FIG. 1, the electrochemical sensing system 100 includes the working electrode 110 and the reference electrode 130 such that the electrochemical sensing system 100 is configured to operate in a two pole sensor system. The reference electrode 130 functions thereby as a pseudo-reference electrode, that is provides a reference voltage for the working electrode 110 to be biased against, as well as communicates electrons to or from the sample (e.g., a liquid or gaseous sample) that includes the target analyte TA. Conventional pseudo-reference electrodes such as, for example, silver/silver chloride (Ag/AgCl) electrodes, generally do not maintain a constant reference voltage. Instead the reference can vary predictably with external conditions, for example, the pH and temperature of the electrolyte can affect the reference potential. If the conditions are known, the potential can be calculated and the electrode can be used as a reference, however, in many cases a calibration measurement has to be performed for reliable measurements. Many conventional pseudo-reference electrodes, for example, Ag/AgCl electrodes, can only operate in limited pH or temperature ranges. Furthermore, many conventional pseudo-reference electrodes (e.g., the Ag/AgCl reference electrode) can be consumed during the electrochemical reaction because the pseudo-reference electrode not only provides a reference voltage for the working electrode, but also communicates electrons to or from the sample. This can lead to oxidation/reduction of the reference electrode material which can eventually be consumed. Thus, conventional reference electrodes generally have a short life.

In contrast, the pseudo-reference electrode 130 described herein, which can be formed from a metal oxide or metal/metal oxide (e.g., oxides of rhodium) can be relatively insensitive to the ambient conditions such as, for example, the pH and temperature, and therefore provide a stable reference voltage. The reference electrode 130 can also be relatively inert such that the reference electrode 130 is not consumed and has a relatively long life. Moreover, the reference electrode 130 can also reduce and/or provide more efficient electron transfer thereby substantially increasing the sensitivity of the electrochemical measurement as compared to a conventional pseudo-reference electrode (e.g., a Ag/AgCl reference electrode).

In some embodiments, the electrochemical sensing system 100 can further include a third counter electrode (not shown). In such embodiments, the electrochemical sensing system 100 can be operated in a three electrode configuration such that the electrons are communicated to or from the sample via the counter electrode. In such embodiments, the reference electrode 130 only serves to provide an electronic reference for the working electrode 110.

The electrical circuit 140 is configured to bias the working electrode 110 at a predetermined operating voltage, for example, a voltage of less than about +0.4V and measure a redox current due to the oxidation or reduction of the target analyte TA or an electroactive by-product of the target analyte TA. In some embodiments, the electrical circuit 140 can include a transimpedance amplifier circuit configured to convert current to an amplified voltage. In some embodiments, the electrical circuit 140 can include an analog to digital converter configured to digitize the input current measurement. For example, the electrical circuit 140 can include a differential analog to digital converter which can increase noise rejection in the voltage measurement. The bias voltage can be communicated into a low end differential input of the analog to digital converter configured to provide a pseudo-negative range. This can, for example, allow digital filtering to remain accurate when noise remains in the low measurement range (e.g., to enhance the limit of detection). In some embodiments, the electrical circuit 140 can include operational amplifiers configured to amplify the measured signal. In some embodiments, the electrical circuit 140 can include a filtering circuit, for example, a low pass filter, a high pass filter, a band pass filter, any other suitable filtering circuit, or combination thereof, configured to substantially reduce signal noise. In some embodiments, the electrical circuit 140 can include a potentiostat circuit, for example, a programmable potentiostat circuit, configured to bias the working electrode 110 at the predetermined voltage. For example, the potentiostat circuit can be configured to bias the working electrode 110 at a biasing voltage in the range of about −0.5 V to about +0.5 V, for example, about −0.4 V, −0.3 V, −0.2 V, −0.1 V, 0 V, +0.1 V, +0.2 V, +0.3 V, or about +0.4 V, inclusive of all ranges therebetween.

In some embodiments, the electrical circuit 140 can include a processor, e.g., a microcontroller, a microprocessor, an ASIC chip, an ARM chip, or a programmable logic controller (PLC). The processor can include signal processing algorithms, for example, band pass filters, low pass filters, any other signal processing algorithms or combination thereof. In some embodiments, the processor can be configured to control the bias voltage in real time, for example, to control one or more parameters of the redox reaction in real time. Such parameters can include, for example, electrochemical reaction rate and dynamic range which can be used to reverse or minimize the effects of electrochemical fouling and/or facilitate real time calibration. In some embodiments, the electrical circuit 140 can include a memory configured to store at least one of a redox current data, bias voltage data, user log, or any other information related to the electrochemical reaction. In some embodiments, the memory can also be configured to store a reference signature, for example, a calibration equation. In such embodiments, the processor can be configured to correlate the measured signal (e.g., the redox current) with the reference signature to determine the concentration of the target analyte TA.

In some embodiments, the electrochemical sensing system 100 can include a communications module (not shown). The communications module can be configured to allow two-way communication with a remote device e.g., a smart phone app, a local computer and/or a remote server. In some embodiments, the communications module can include a communication interface to provide wired communication with the external device, e.g., a USB or FireWire interface. In some embodiments, the communications module can include means for wireless communication with the external device, e.g., Wi-Fi, Bluetooth®, ANT+, low powered Bluetooth®, Zigbee and the like. In some embodiments, the communications module can include a RFID chip configured to store information, for example, the reference signature or sensing history, and allow a near field communication (NFC) device to read the stored information and/or update the stored information. In some embodiments, the electrochemical sensing system 100 can include a power source, for example, a rechargeable battery, configured to power the electrical circuit 140, the communications module or any other electronic component included in the electrochemical sensing system 100.

In some embodiments, the communications module can include a display configured to communicate information to the user, e.g., history of use, remaining battery life, wireless connectivity status, and/or visual reminders. In some embodiments, the communications module can also include microphones and/or vibration mechanisms to convey audio and tactile alerts. In some embodiments, the communications module can include a means for user input, e.g., a button, a switch, and/or a touch screen, to provide an interface for input of at least one of power ON/OFF the electrochemical sensing system 100, reset the electrochemical sensing system 100, trigger communication between the electrochemical sensing system 100 and an external device, e.g., smart phone.

In some embodiments, the electrochemical sensing system 100 can be disposed in a housing (not shown) configured to house the components of the electrochemical sensing system 100. In some embodiments, the electrochemical sensing system 100 can be fixedly disposed in the housing. In some embodiments, one or more components of the electrochemical sensing system 100, for example, the working electrode 110 and/or the reference electrode 130 can be removably disposed in the housing. In such embodiments, the working electrode 110 and the reference electrode 130 can be configured to be replaced. In some embodiments, the housing can be substantially small such that the electrochemical sensing system 100 can be mounted on a user, for example, the skin of a user via an adhesive. For example, the housing can be configured to allow the working electrode 110 (and the biological sensor 120) and the reference electrode 130 to pierce through the skin of a user and contact a bodily fluid, for example, blood, or interstitial fluid. The electrochemical sensing system 100 can thereby, be used to measure the concentration of a target analyte TA in the bodily fluid of the user in real time, for example, to provide real time health monitoring (e.g., glucose monitoring).

Having described above various general principles, several embodiments of these concepts are now described. These embodiments are only examples, and many other configurations an electrochemical sensing system are contemplated.

Figure 2:
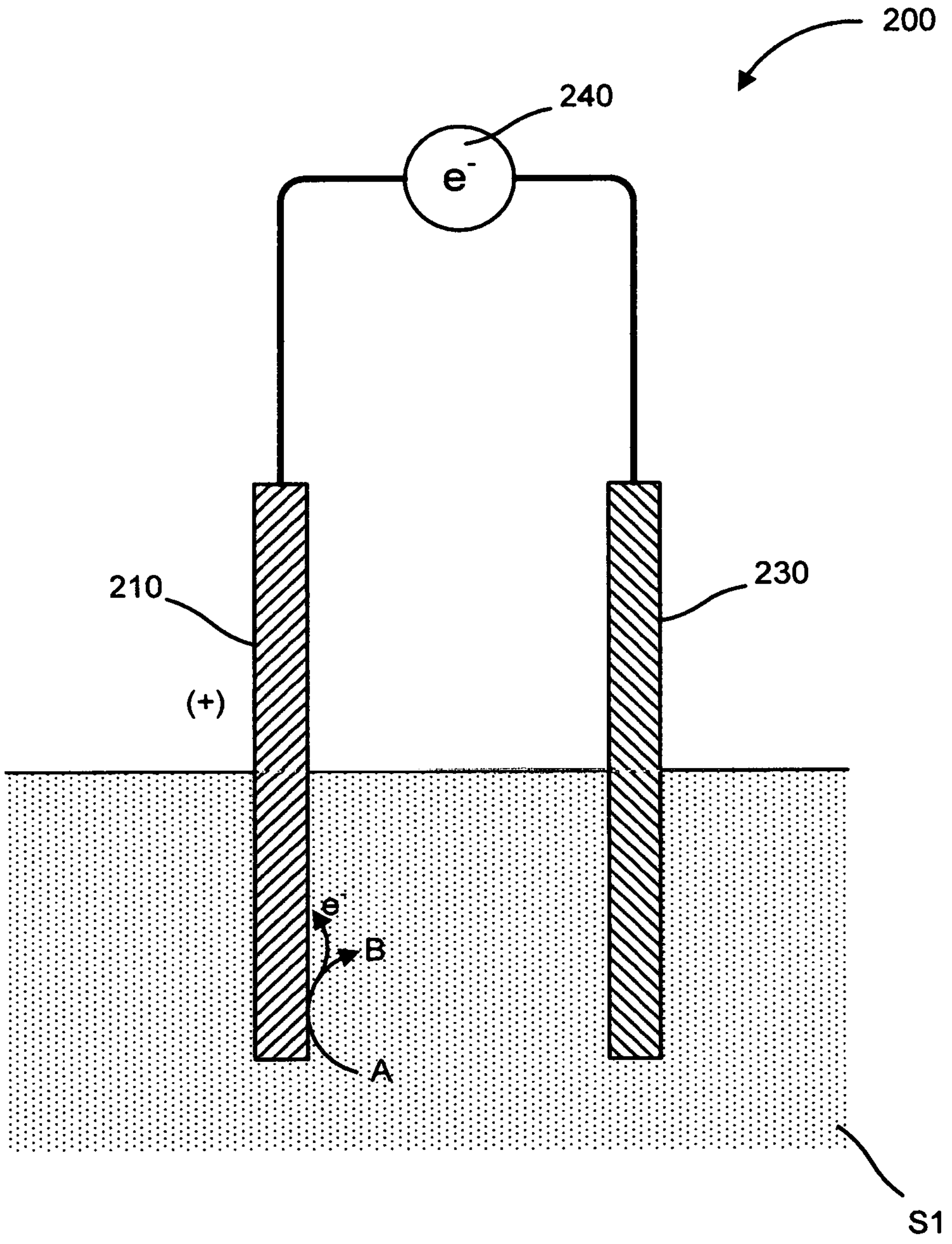
FIG. 2 is a schematic illustration of an electrochemical sensing system, according to an embodiment.

In some embodiments, an electrochemical sensing system can be configured to sense a target analyte which is electroactive. Referring now to FIG. 2, an electrochemical sensing system 200 includes a working electrode 210, a reference electrode 230 and an electrical circuit 240. The electrochemical sensing system 200 can be configured to interact with a sample S1 to determine a concentration of an electroactive target analyte A included in the sample S1.

The working electrode 210 can include a rhodium electrode, or an electrode having rhodium disposed thereon. The working electrode 210 can be configured to oxidize the target analyte A at an operating voltage of less than about 0.4 V such that at least one of an oxidation and reduction of one or more interfering species on the working electrode is substantially reduced. In some embodiments, the biasing voltage can be, less than about 0.35 V, less than about 0.3 V, less than about 0.25 V, less than about 0.20 V, less than about 0.15 V, less than about 0.1 V, less than about 0.05 V, or about 0 V, inclusive of all ranges therebetween. The bias voltage can be substantially low such that interfering electroactive species that can also be included in the sample S1, are not oxidized or reduced on the working electrode 210. In some embodiments, the working electrode 210 can be formed from an oxide of rhodium, for example rhodium dioxide. In some embodiments, a blend of rhodium and another metal, for example, ruthenium, platinum, palladium, gold, nickel, any other suitable metal or alloy, can be used to form the working electrode 210. In some embodiments, the working electrode can include a substrate on which rhodium is disposed, for example, chromium, titanium, nitinol, gold, platinum, nickel, palladium, stainless steel, any other suitable material or combination thereof. While shown as being a cylindrical rod, the working electrode 210 can have any shape or size. The working electrode 210 can be substantially similar to the working electrode 110 described with respect to the electrochemical sensing system 100, and is therefore not described in further detail herein.

The reference electrode 230 is electronically coupled to the working electrode 210 via the electrical circuit 240. The electrochemical sensing system 200 is configured to operate in a 2 pole sensor configuration, such that the reference electrode 230 can operate as a pseudo-reference electrode. The reference electrode 230 can include any suitable reference electrode that can provide a stable reference voltage for the working electrode 210 in the two electrode configuration and does not get consumed by the oxidation or reduction reaction, thereby providing longer shelf life, no usage limitations due to reference consumption, and substantially reduce signal drift. Suitable materials for the reference electrode 230 can include, for example, metal oxides (e.g., iridium oxide, platinum oxide, palladium oxide, ruthenium oxide), conducting polymers (e.g., polyethylene dioxythiophene:polystyrene sulfonate (PEDOT:PSS), any other suitable stable reference electrode or combination thereof. In some embodiments, the reference electrode 230 can include a rhodium and its oxides (e.g., $RhO_2$, $Rh(OH)_3$, $Rh_2O_3$, etc.). In some embodiments, the reference electrode 230 can include iridium and its oxides. In some embodiments, the reference electrode 230 can include palladium and its oxides. The reference electrode 230 can be substantially similar to the reference electrode 130 described with respect to the electrochemical sensing system 100, and is therefore not described in further detail herein.

The electrical circuit 240 is configured to bias the working electrode 210 at a predetermined operating voltage, for example, a voltage of less than about 0.4V and measure a redox current due to the oxidation or reduction of the electroactive target analyte A. The electrical circuit 240 can be substantially similar to the electrical circuit 140 included in the electrochemical sensing system 100 and is therefore, not described in further detail herein. In some embodiments, the components of the electrochemical sensing system 200 can be disposed in a housing. The housing can substantially similar to the housing described with respect to the electrochemical sensing system 100, and is therefore not described in further detail herein.

The sample S1 can be any sample which contains the target analyte A. For example, the sample S1 can be a liquid sample such as, for example, a beverage, an environmental sample, a food sample, an agricultural sample, or a bodily fluid such as, for example, blood, urine, fecal matter solution, saliva, interstitial fluid, synovial fluid, cerebral fluid, sweat, or tear drops. The sample S1 can be an in vitro sample, for example, disposed in a test container. In some embodiments, the sample S can be an in vivo sample, for example, a bodily fluid inside the body of a user (e.g., blood, interstitial fluid). As shown in FIG. 2, the sample S1 includes the electroactive target analyte A. The working electrode 210 is biased at a predetermined biasing voltage, for example, a biasing voltage of less than about 0.3V. The target analyte A can diffuse to the surface of the working electrode 210 and oxidize on the surface of the electrode. The oxidation produces a non-electroactive by-product B (or a by-product non-electroactive at 0.3 V) and an electron $e^-$ which is communicated through the positively charged working electrode to the electrical circuit 240 such that the oxidation current is measured. For example, the target analyte A can be $H_2O_2$ which oxidizes at the working electrode 210 via the following electrochemical reaction:

$$H_2O_2 \xrightarrow[\text{Rhodium}]{+0.3\text{ V}} O_2 + 2H^+ + 2e^-$$

In some embodiments, the working electrode 210 can be biased at negative voltage for example, a voltage of greater than about −0.5 V. The target analyte A can, for example, reduce at the working electrode 210 at this biasing voltage and accept an electron from the negatively charged working electrode 210.

Figure 3:
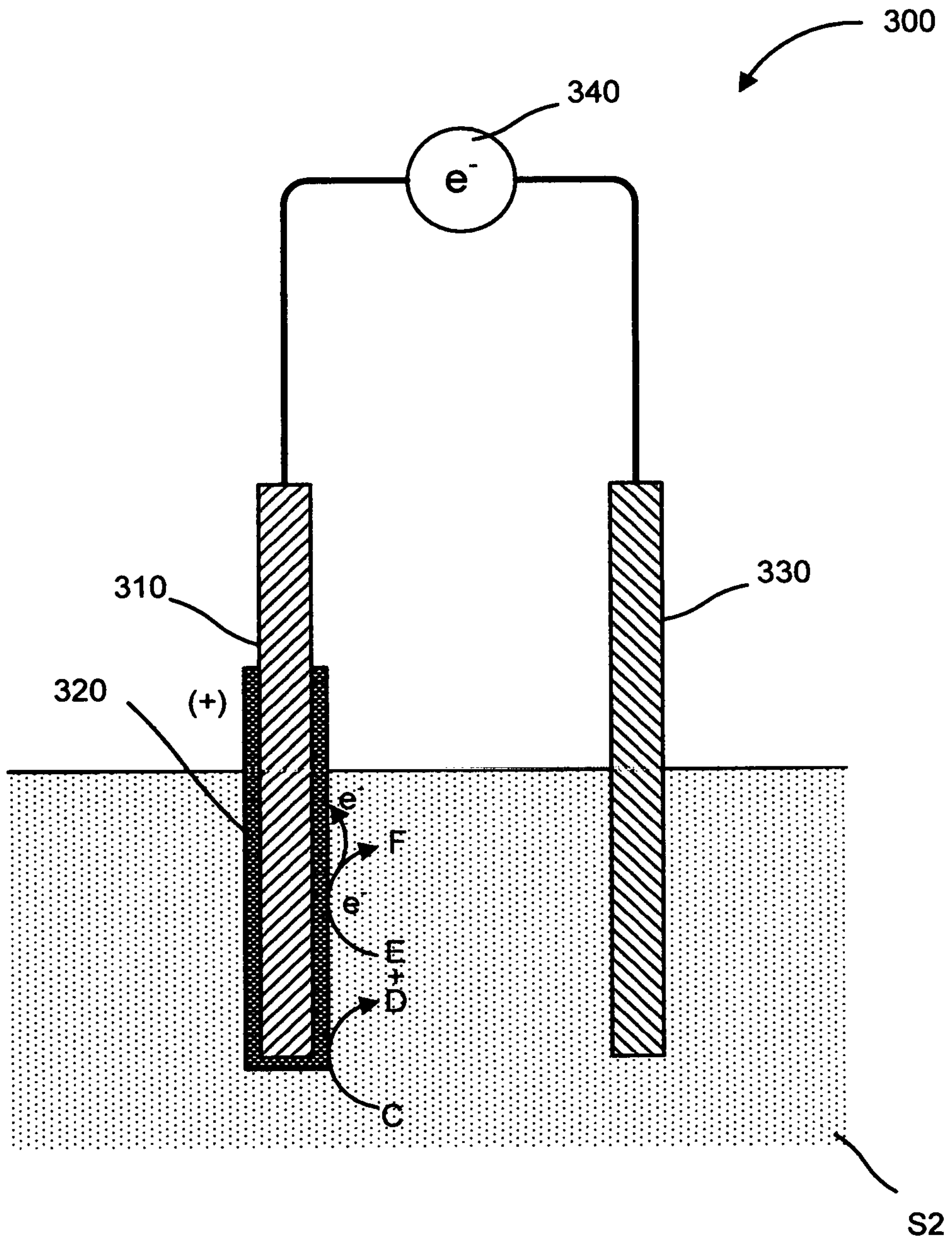
FIG. 3 is a schematic illustration of an electrochemical sensing system, according to an embodiment.

In some embodiments, an electrochemical sensing system can be configured to sense a target analyte which can be a non-electroactive biomolecule. Referring now to FIG. 3, an electrochemical sensing system 300 includes a working electrode 310, a biosensing molecule 320, a reference electrode 330 and an electrical circuit 340. The electrochemical sensing system 300 can be configured to interact with a sample S2 to determine a concentration of a non-electroactive target analyte C included in the sample S2.

The working electrode 310 can include a rhodium electrode, or an electrode having rhodium disposed thereon. The working electrode 310 can be configured to oxidize the electrochemical by-product E of the target analyte C at a biasing voltage of less than about 0.4 V such that at least one of an oxidation and reduction of one or more interfering species on the working electrode is substantially reduced. In some embodiments, the biasing voltage can be, less than about 0.35 V, less than about 0.3 V, less than about 0.25 V, less than about 0.20 V, less than about 0.15 V, less than about 0.1 V, less than about 0.05 V, or about 0 V, inclusive of all ranges therebetween. The bias voltage can be substantially low such that interfering electroactive species, that can also be included in the sample S2, are not oxidized or reduced on the working electrode 310. In some embodiments, the working electrode 310 can be formed from an oxide of rhodium, for example rhodium dioxide. In some embodiments, a blend of rhodium and another metal, for example, ruthenium, platinum, palladium, gold, nickel, any other suitable metal or alloy, can be used to form the working electrode 310. The working electrode 310 can be substantially similar to the working electrode 110 described with respect to the electrochemical sensing system 100, and is therefore not described in further detail herein.

As shown in FIG. 3, the biosensing molecule 320 is disposed on the surface of the working electrode 310. The target analyte C can include a biomolecule which is non-electroactive. Such target analytes C can include, for example, glucose, sucrose, glutamate, lactate, cholesterol, alcohol, aspartate transaminase, alkaline transaminase, alkaline phosphatase, urea, ketones or any other biomolecule. The biosensing molecule 320 can be configured to catalytically decompose the non-electroactive target analyte C and yield an electroactive by-product E. The electroactive by-product E can thus, be oxidized or reduced at the working electrode 310 to yield a current which corresponds to the concentration of the target analyte C. In some embodiments, the biosensing molecule 320 can be an enzyme such as, for example, glucose oxidase, glutamate oxidase, lactate oxidase, lactate dehydrogenase, cholesterol oxidase, invertase, urease, any other suitable enzyme or combination thereof. In some embodiments, a plurality of biosensing molecules 320 can be disposed on the working electrode 310. For example, a first biosensing molecule can decompose the non-electroactive target analyte C into intermediate non-electroactive by-products. A second biosensing molecule can then decompose at least one of the intermediate non-electroactive by-products to yield a final electroactive by-product. In this manner, one, two, three or even more biosensing molecules can be disposed on the working electrode which can sequentially dispose the target analyte C and its redox by-products to yield the final electroactive by-product. In some embodiments, the biosensing molecule 320 can be a synthetic redox-active receptor, for example, a viologen or a conjugated pyridinium. In some embodiments, a mediator or a transducer can be included with the biosensing molecule 320.

The biosensing molecule 320 can be disposed on the surface of the working electrode 310 using any suitable means. In some embodiments, the biosensing molecule 310 can be physically adsorbed on the surface. In some embodiments, the biosensing molecule 320 can be covalently coupled to the surface of the rhodium on the working electrode 310, for example, using thiol chemistry. In some embodiments, the biosensing molecule 320 can be suspended in a porous membrane, for example, a polyurethane membrane, a glutaraldehyde membrane, a sol-gel membrane, a NAFION® membrane, any other suitable membrane or combination thereof.

In some embodiments, the biosensing molecule 320 can include a synthetic redox-active receptor, for example, a viologen or a conjugated pyridinium. The synthetic redox-active receptor can be configured to be moved between different electronic states. For example, the synthetic redox-active receptor can bind or otherwise interact with the target analyte C resulting in a change in reduction potential. The binding or otherwise interaction of the synthetic redox-active receptor with the target analyte C can be an equilibrium reaction in which the target analyte C does not decompose. The synthetic redox-active receptor can then communicate change in electronic state to the working electrode 310. This generates a current which can be measured by the electrical circuit 240, as described herein. In this manner a synthetic redox-active receptor can be used to electrochemically sense the target analyte C, without the target analyte C being consumed. Such synthetic redox-active receptors can have a higher stability than biomolecules. Thus, they can allow for better stability, lesser drift and longer lifetime of the working electrode 310.

The reference electrode 330 is electronically coupled to the working electrode 310 via the electrical circuit 340. The electrochemical sensing system 300 is configured to operate in a 2 pole sensor configuration, such that the reference electrode 330 can operate as a pseudo-reference electrode. The reference electrode 330 can include any suitable reference electrode that can provide a stable reference voltage for the working electrode 310 in the two electrode configuration and does not get consumed by the oxidation or reduction reaction, thereby providing longer shelf life, no usage limitations due to reference consumption, and substantially reduce signal drift. In some embodiments, the reference electrode 330 can include rhodium and its oxides (e.g., $RhO_2$, $Rh(OH)_3$, $Rh_2O_3$, etc.). In some embodiments, the reference electrode 330 can include iridium and its oxides. In some embodiments, the reference electrode can include palladium and its oxides. The reference electrode 330 can be substantially similar to the reference electrode 130 described with respect to the electrochemical sensing system 100, and is therefore not described in further detail herein.

The electrical circuit 340 can be configured to bias the working electrode 310 at a predetermined operating voltage, for example, a voltage of less than about 0.4V and measure a redox current due to the oxidation or reduction of the electroactive target analyte C. The electrical circuit 340 can be substantially similar to the electrical circuit 140 described with respect to the electrochemical sensing system 100, and is therefore not described in further detail herein.

In some embodiments, the components of the electrochemical sensing system 300 can be disposed in a housing. The housing can be substantially similar to the housing described with respect to the electrochemical sensing system 100, and is therefore not described in further detail herein.

The sample S2 can be any sample which contains the target analyte C. For example, the sample S2 can be a liquid sample, for example, a beverage, an environmental sample, a food sample, an agricultural sample, or a bodily fluid such as, for example, blood, urine, fecal matter solution, saliva, interstitial fluid, synovial fluid, cerebral fluid, sweat, tear drops, or any other bodily fluid. The sample S2 can be an in vitro sample, for example, disposed in a test container. In some embodiments, the sample S2 can be an in vivo sample, for example, a bodily fluid inside the body of a user (e.g., blood, interstitial fluid). As shown in FIG. 3, the sample S2 includes the non-electroactive target analyte C. The working electrode 310 is biased at a predetermined positive voltage, for example, a biasing voltage of less than about 0.3V. The non-electroactive target analyte C can be catalytically decomposed by the biosensing molecule 320 to yield a non-electroactive by-product D and an electroactive by-product E. The electroactive by-product E can diffuse to the surface of the working electrode 310 where it can oxidize to generate a by-product F and an electron $e^-$ which is communicated through the positively charged working electrode 310 to the electrical circuit 340 and measured as a current.

For example, the target analyte C can be glucose which is non-electroactive and the biosensing molecule 320 can be glucose oxidase (or a synthetic biosensing molecule such as, for example, a viologen or a conjugated pyridinium). The glucose oxidase can enzymatically decompose the glucose to yield gluconic acid (non-electroactive by-product D) and hydrogen peroxide (electroactive by-product E) as shown in the following reaction:

$$\text{Glucose} + O_2 \xrightarrow{\text{Glucose oxidase}} \text{Gluconic acid} + H_2O_2$$

The hydrogen peroxide can diffuse to the surface of the working electrode 310 and be oxidized on the working electrode 310 at a low bias voltage, for example, less than about +0.3 V to produce a current, which corresponds to the concentration of the glucose.

Figure 4:
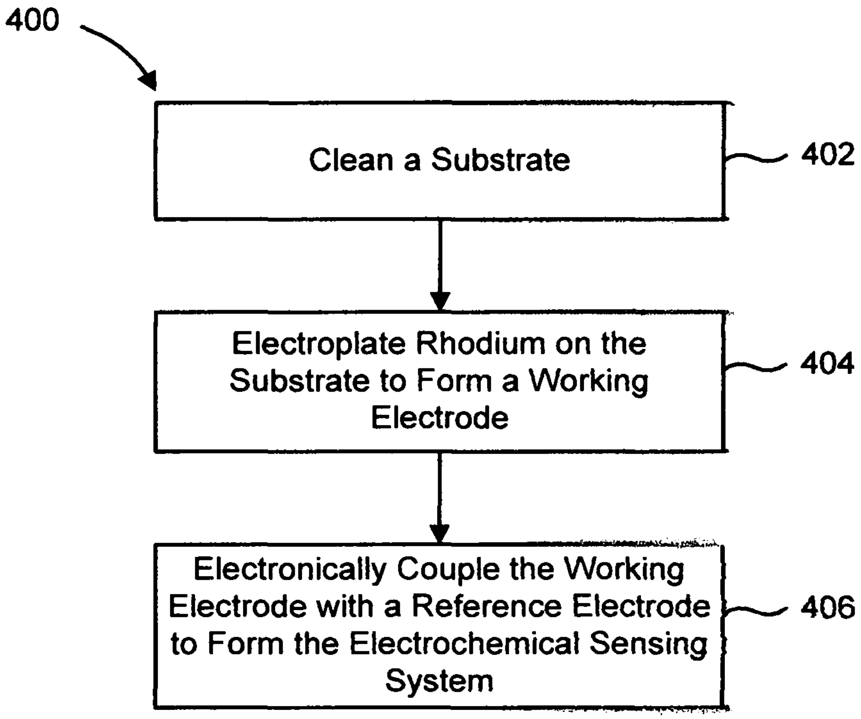
FIG. 4 is a schematic flow diagram showing a method of disposing rhodium on a substrate, according to an embodiment.

FIG. 4 illustrates a flow diagram showing an exemplary method 400 for forming a working electrode, for example, the working electrode 100, 200, 300 or any other working electrode described herein, using electroplating. First, a substrate is cleaned 402. The substrate can be formed from any suitable conductive material that has good adhesion with rhodium, for example, chromium, titanium, nitinol, gold, platinum nickel, palladium, stainless steel, any other suitable material or combination thereof. In some embodiments, the substrate can be cleaned with one or more solvents such as, for example, acetone, ethanol, methanol, isopropyl alcohol, any other suitable solvent or combination thereof. In some embodiments, the substrate can be cleaned by immersing in an alkaline solution, for example, a sodium hydroxide (NaOH) solution, a potassium hydroxide (KOH) solution, a tetramethyl ammoniumhydroxide (TMAH) solution, any other alkaline solution or a combination thereof. In some embodiments, the substrate can be cleaned by immersing in an acidic solution, for example, a sulfuric acid solution, hydrochloric acid solution, hydrofluoric acid solution, nitric acid solution, aqua regia, any other acidic solution or a combination thereof. In some embodiments, the alkaline and/or acidic solution cleaning can be enhanced by biasing the substrate at a positive or negative voltage while immersed in the alkaline or the basic solution, or cycling the voltage between a predetermined positive and negative voltage. After the substrate is cleaned, rhodium is electroplated on the substrate to form the working electrode 404. Rhodium can be electroplated by applying a positive biasing voltage on the substrate while being immersed in a rhodium salt solution, for example, a rhodium sulfate ($Rh_2(SO)_3$) solution, a rhodium chloride solution, any other rhodium salt solution or a combination thereof. The thickness and/or morphology of the rhodium metal electroplated on the substrate can be varied by controlling the biasing voltage or the time for which electroplating is performed. The working electrode is then electronically coupled with a reference electrode 406, for example, the reference electrode 130, 230, 330, or any other reference electrodes described herein. The electronic coupling can be performed via an electrical circuit configured to bias the working electrode at a predetermined biasing voltage and measure a redox current. The electrical circuit can include, for example, the electrical circuit 140, 240, 340, or any other electrical circuit described herein.

Figure 5:
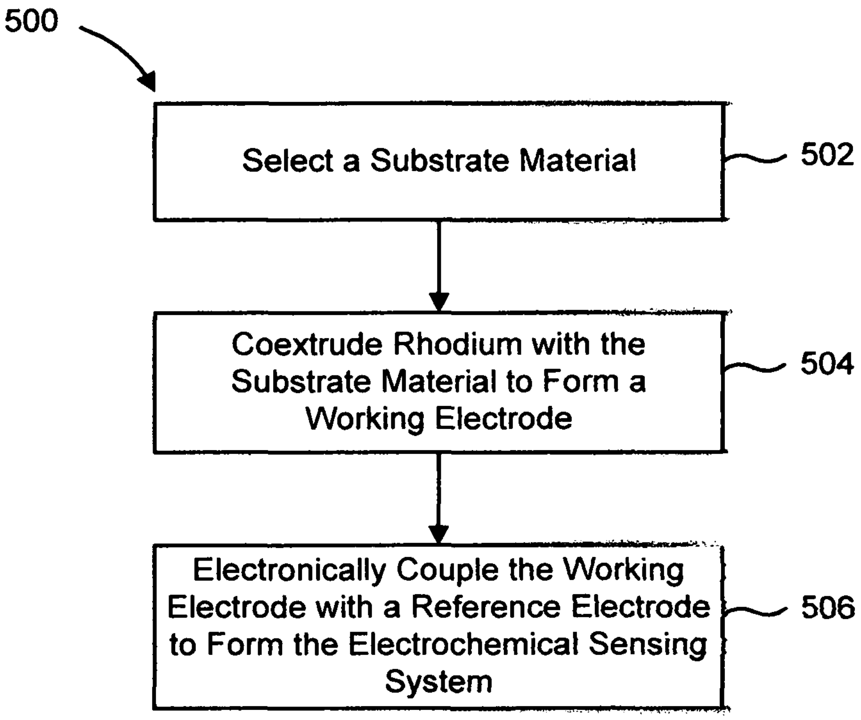
FIG. 5 is a schematic flow diagram showing a method of disposing rhodium on a substrate, according to an embodiment.

FIG. 5 illustrates a flow diagram showing an exemplary method 500 of forming a working electrode, for example, the working electrode 100, 200, 300 or any other working electrode described herein, using co-extrusion. First, a substrate material is selected 502. The substrate material can be any suitable conductive material that has good adhesion with rhodium, for example, chromium, titanium, nitinol, gold, platinum nickel, palladium, stainless steel, any other suitable material or combination thereof. Next rhodium is coextruded with the substrate material such that a rhodium layer of a predetermined thickness is disposed over the substrate to form the working electrode 504. The working electrode is then electronically coupled with a reference electrode, for example, the reference electrode 130, 230, 330, or any other reference electrodes described herein 506. The electronic coupling can be performed via electrical circuit configured to bias the working electrode at a predetermined biasing voltage and measure a redox current. The electrical circuit can include, for example, the electrical circuit 140, 240, 340 or any other electrical circuit described herein.

Figure 6:
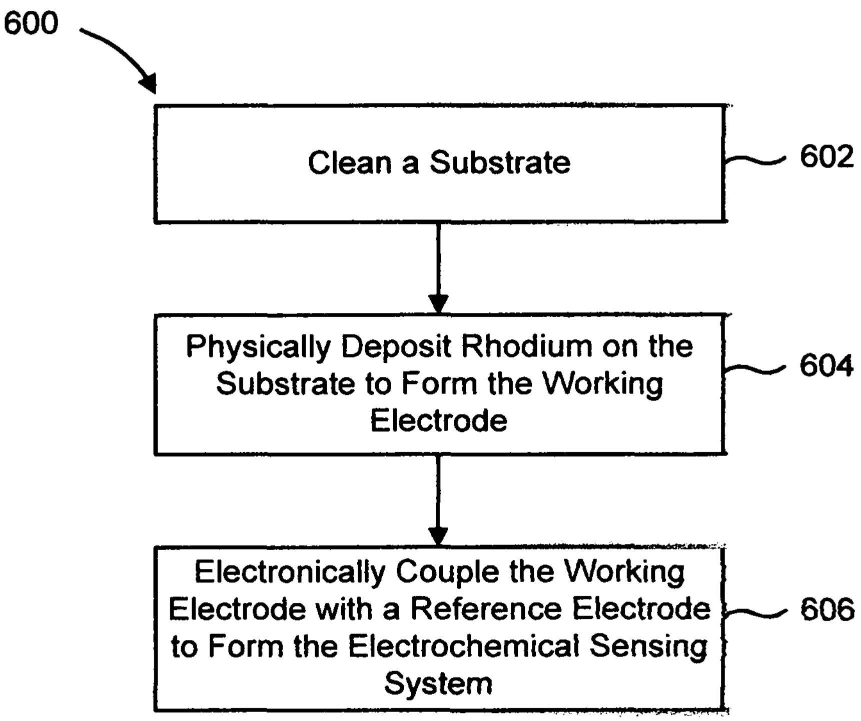
FIG. 6 is a schematic flow diagram showing a method of disposing rhodium on a substrate, according to an embodiment.

FIG. 6 illustrates a flow diagram showing an exemplary method 600 of forming a working electrode, for example, the working electrode 100, 200, 300 or any other working electrode described herein, using physical deposition of rhodium. First, a substrate is cleaned 602. The substrate can be formed from any suitable conductive material that has good adhesion with rhodium, for example, chromium, titanium, nitinol, gold, platinum nickel, palladium, stainless steel, any other suitable material or combination thereof. The cleaning can be performed using solvents, alkaline solutions or basic solutions, as described with respect to method 400, and is therefore not described in further detail herein. After the substrate is cleaned, rhodium is physically deposited on the substrate to form the working electrode 604. Such processes can include, for example, casting or a physical vapor deposition (PVD) process such as, for example, e-beam evaporation, thermal evaporation, sputtering, atomic layer deposition (ALD), pulsed laser deposition (PLD), any other physical vapor deposition process or a combination thereof. The working electrode is then electronically coupled with a reference electrode, for example, the reference electrode 130, 230, 330, or any other reference electrodes described herein 606. The electronic coupling can be performed via an electrical circuit configured to bias the working electrode at a predetermined biasing voltage and measure a redox current. The electrical circuit can include, for example, the electrical circuit 140, 240, 340, or any other electrical circuit described herein.

Figure 7:
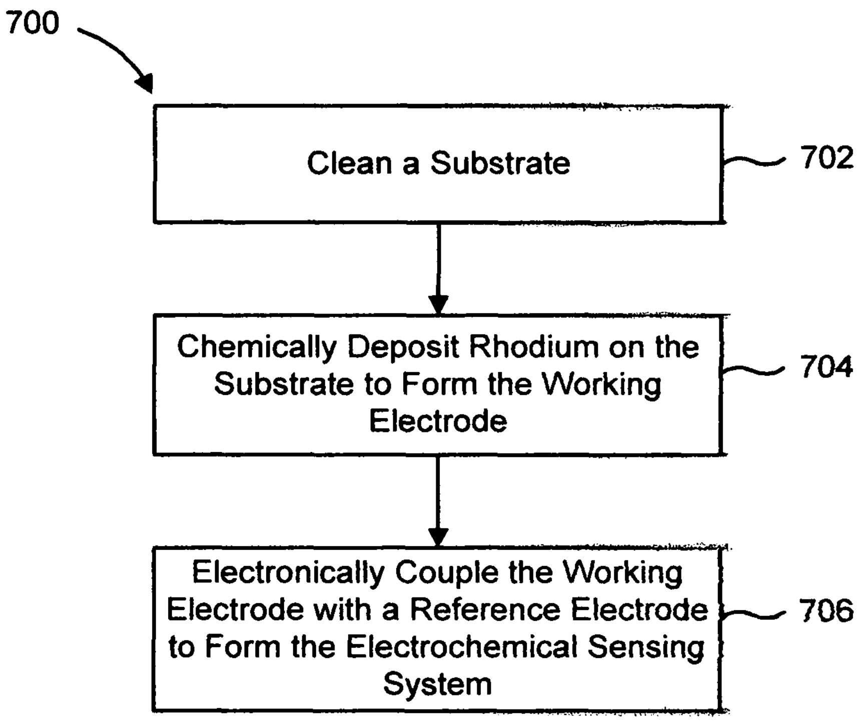
FIG. 7 is a schematic flow diagram showing a method of disposing rhodium on a substrate, according to an embodiment.

FIG. 7 illustrates a flow diagram showing an exemplary method 700 of forming a working electrode, for example, the working electrode 100, 200, 300 or any other working electrode described herein, using chemical deposition of rhodium. First, a substrate is cleaned 702. The substrate can be formed from any suitable conductive material that has good adhesion with rhodium, for example, chromium, titanium, nitinol, gold, platinum nickel, palladium, stainless steel, any other suitable material or combination thereof. The cleaning can be performed using solvents, alkaline solutions or basic solutions, as described with respect to method 400, and is therefore not described in further detail herein. After the substrate is cleaned, rhodium is chemically deposited on the substrate to form the working electrode 704. Such processes can include, for example, low pressure chemical vapor deposition (LPCVD), plasma enhanced chemical vapor deposition (PECVD), molecular beam epitaxy (MBE), any other suitable chemical vapor deposition process or combination thereof. The working electrode is then electronically coupled with a reference electrode, for example, the reference electrode 130, 230, 330, or any other reference electrodes described herein 706. The electronic coupling can be performed via an electrical circuit configured to bias the working electrode at a predetermined biasing voltage and measure a redox current. The electrical circuit can include, for example, the electrical circuit 140, 240, 340, or any other electrical circuit described herein.

FIG. 8 shows a flow diagram 800 of an exemplary method of forming an electrochemical sensing system and using the system for electrochemical sensing. First, a substrate is cleaned with a solvent solution 802. The substrate can be formed from any suitable conductive material that has good adhesion with rhodium, for example, chromium, titanium, nitinol, gold, platinum nickel, palladium, stainless steel, any other suitable material or combination thereof. The substrate is then cleaned in an alkaline solution 804, for example, a sodium hydroxide (NaOH) solution, a potassium hydroxide KOH) solution, a tetramethyl ammoniumhydroxide (TMAH) solution, any other alkaline solution or a combination thereof. Next the substrate is cleaned by immersing in an acidic solution 806, for example, a sulfuric acid solution, hydrochloric acid solution, hydrofluoric acid solution, nitric acid solution, aqua regia, any other acidic solution or a combination thereof. In some embodiments, the alkaline and/or acidic solution cleaning can be enhanced by biasing the substrate at a positive or negative voltage while immersed in the alkaline or the basic solution, or cycling the voltage between a predetermined positive and negative voltage. Rhodium is then electroplated on the substrate to form the working electrode 808. Rhodium can be electroplated by applying a positive biasing voltage on the substrate while being immersed in a rhodium salt solution, for example, a rhodium sulfate (Rh2(SO)3) solution, a rhodium chloride solution, any other rhodium salt solution or a combination thereof. The thickness and/or morphology of the rhodium metal electroplated on the substrate can be varied by controlling the biasing voltage or the time for which electroplating is performed.

Optionally, a biosensing molecule can be disposed on the working electrode 810. The biosensing molecule can include any biosensing molecule and can be disposed in any suitable manner as described with respect to the biosensing molecule 130 included in the electrochemical sensing system 100, described herein. The working electrode is then electronically coupled with a reference electrode 812, for example, the reference electrode 130, 230, 330, or any other reference electrode described herein. The electronic coupling can be performed via an electrical circuit configured to bias the working electrode at a predetermined biasing voltage and measure a redox current. The electrical circuit can include, for example, the electrical circuit 140, 240, 340, or any other electrical circuit described herein. The working electrode and the reference electrode are immersed in a sample that includes a target analyte whose concentration is being measured 814. The working electrode is biased at predetermined voltage to oxidize or reduce the target analyte or an electroactive by-product of the target analyte (e.g., produced by catalytic decomposition of the target analyte by the biosensing molecule) and the redox current is measured 816. The measured current is compared with a reference signature, for example, a calibration plot, or a calibration equation to determine the concentration of the target analyte in the sample 818.

The following example shows a method of forming a rhodium working electrode that includes glucose oxidase molecule disposed thereon. The working electrode is included in an electrochemical sensing system and used to electrochemically measure the concentration of glucose in the presence of interferents. This example is only for illustrative purposes and is not intended to limit the scope of the present disclosure.

Rhodium Working Electrode Based Glucose Sensor

Figure 9:
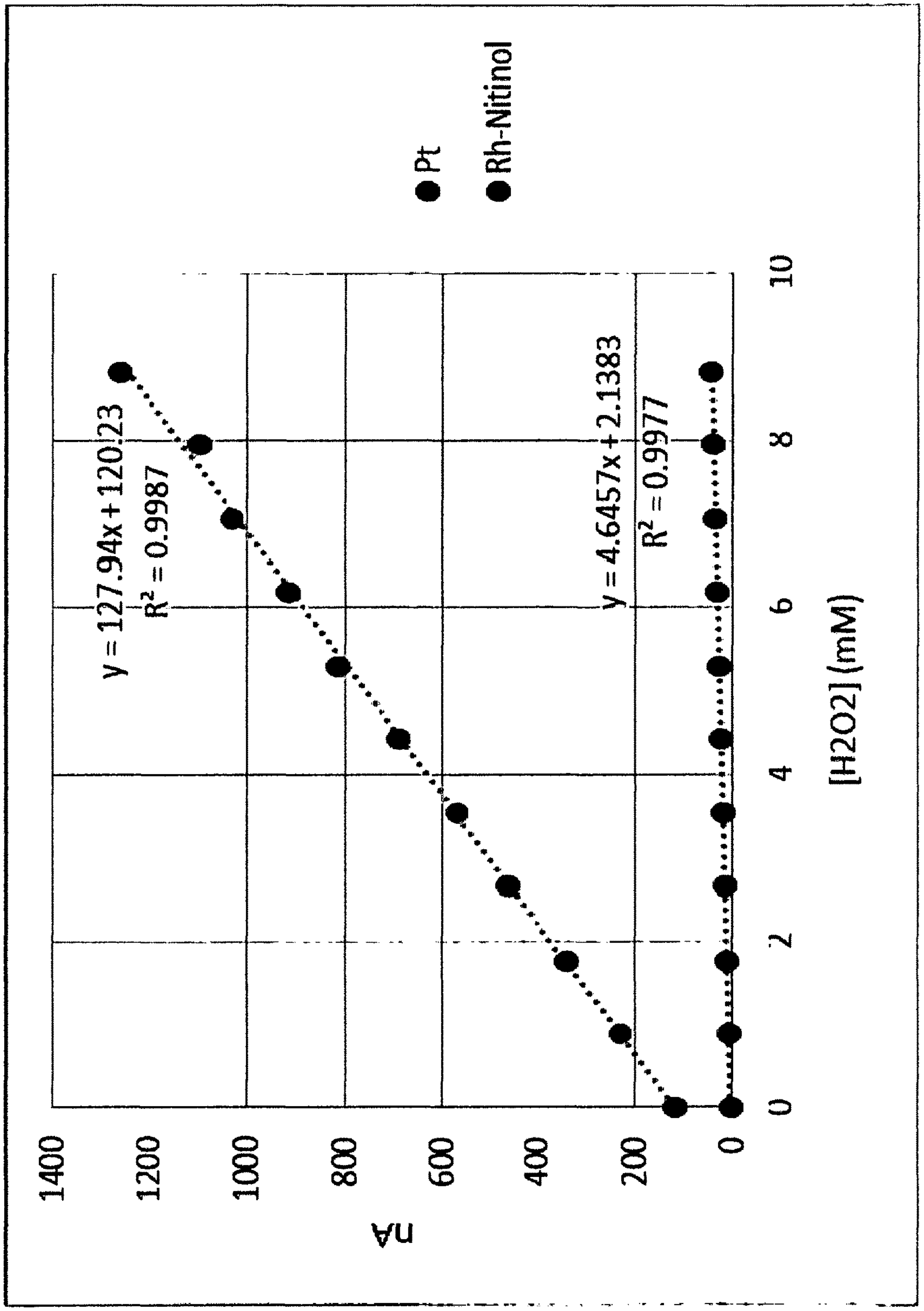
FIG. 9 is a plot showing the sensitivities of a rhodium working electrode and a platinum working electrode towards sensing hydrogen peroxide.

A 0.004 inch diameter nitinol wire was electroplated with rhodium. The nitinol wire was cleaned with acetone and 70% isopropanol and dried with air or nitrogen. The nitinol wire was further cleaned in a NaOH solution by biasing the nitinol wire at a voltage in the range of about 3 V to about 6 V in the NaOH solution for about 1 min, and then rinsed with deionized (DI) water. The nitinol wire was immersed in an acid dip solution (RioGrande, NM) for a short time and then rinsed with DI water. The nitinol wire was then immersed in a $Rh_2(SO)_3$ electroplating solution (RioGrande, NM) and biased at a voltage in the range of about 3 V to about 6 V for about 10 seconds to electroplate rhodium on the working electrode. The coated wire length was about 1-10 mm from a distal end of the nitinol wire. At this depth, an electroplating current of about 0.04 A to about 0.07 A was generated. After the electroplating process, the rhodium plated nitinol wire was rinsed in DI water. The electrochemical performance of the rhodium plated nitinol wire (also referred to as "the rhodium working electrode") was tested at a 0.3 V biasing voltage and compared with the electrochemical performance of a platinum wire biased at 0.6 V. FIG. 9 shows the sensitivity of the rhodium working electrode and platinum electrode. The rhodium working electrode had a sensitivity towards hydrogen peroxide of about 127.94 nA/mM. This was substantially higher than the sensitivity of the platinum electrode towards hydrogen peroxide which was about 4.65 nA/mM.

Figure 10:
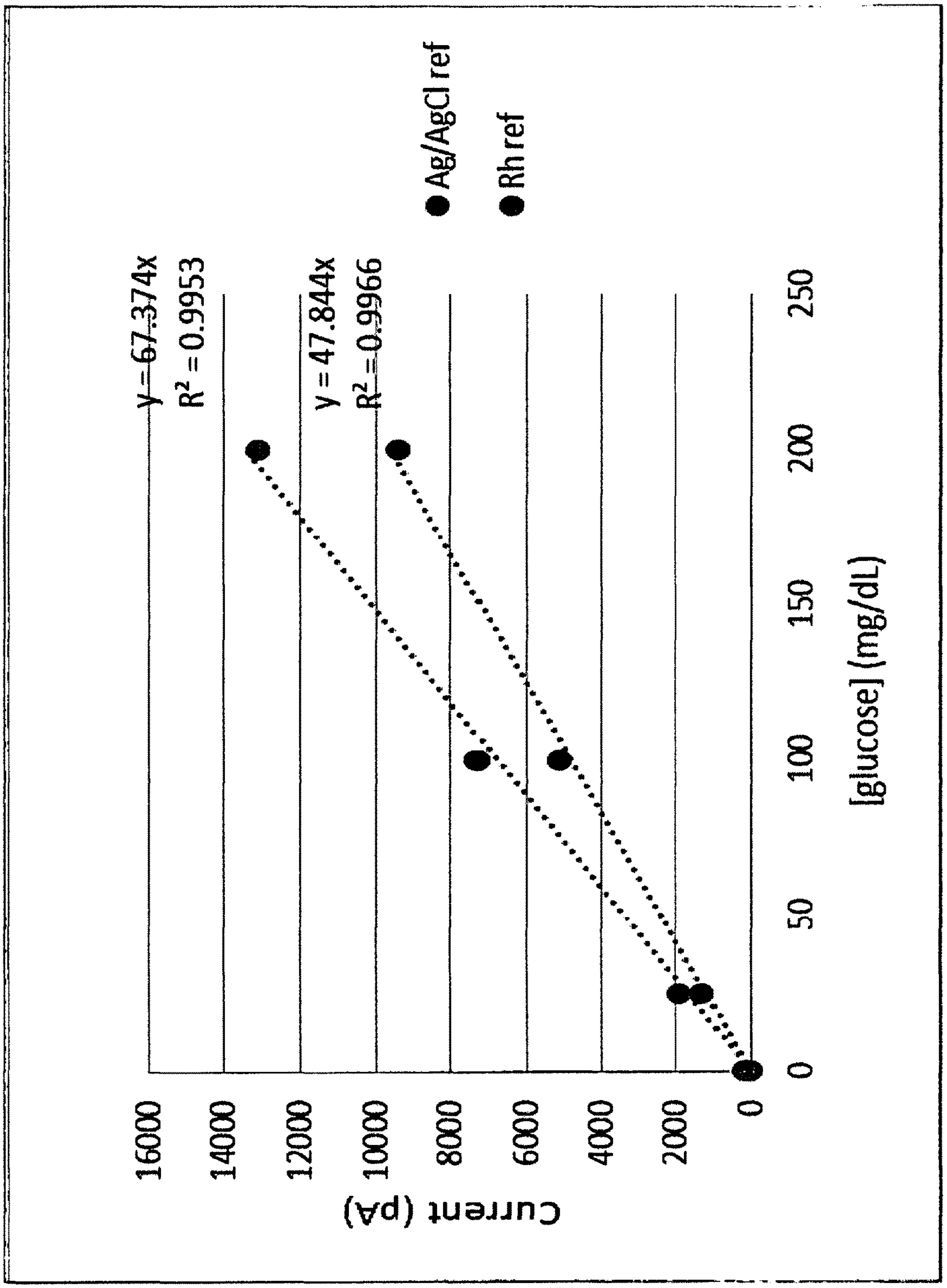
FIG. 10 is a plot showing the sensitivity of a glucose sensor that includes a glucose oxidase coated rhodium working electrode towards sensing glucose

The rhodium working electrode was coated with an ultra violet (UV) activated polyurethane and glucose oxidase solution which includes 1372 mg Alberdingk® Boley 484, 1372 mg Alberdingk® Boley U2101, 27 mg Doublecure 73W, 371 μL BBI enzymes 500 kU glucose oxidase solution, and 50 μL 25% glutaraldehyde solution. The solution was UV cured for 10 seconds under a carbon dioxide atmosphere. The glucose oxidase coated rhodium working electrode was tested at a biasing voltage of about +0.3 V in about 0-400 mg/dL glucose solution and demonstrated a sensitivity of about 67 pA/mg/dL. The electrochemical performance of the rhodium plated nitinol wire (also referred to as "the rhodium working electrode") was tested at a 0.3 V biasing voltage against a rhodium oxide reference and compared with the electrochemical performance using a Ag/AgCl reference. FIG. 10 shows the sensitivity of rhodium working electrode towards glucose when tested against the rhodium oxide reference electrode and the Ag/AgCl reference electrode. The rhodium reference electrode gave greater sensitivity (67 pA/mg/dL) at the low biasing voltage compared to the Ag/AgCl reference (49 pA/mg/dL) at the same bias voltage. Furthermore, the performance of the working electrode was substantially unaffected by interferents including ascorbic acid, uric acid, and acetaminophen.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

We claim:

1. An electrochemical sensing system, comprising:

a working electrode, wherein the working electrode is platinum, wherein said working electrode comprises a porous membrane, said porous membrane configured to at least one of control the diffusion of the target analyte to the surface of the working electrode and prevent biofouling of the working electrode;

a reference electrode, wherein the reference electrode is iridium;

a housing, wherein said housing is configured to house said working and said reference electrodes and to allow for insertion of said working and said reference electrodes, through the use of a needle or penetration device, into a biofluid within a human or animal for sensing, wherein said working electrode and reference electrodes are removable from said housing for replacement;

and an electrical circuit electronically coupled to the working electrode and the reference electrode, the electrical circuit configured to: (a) provide a constant bias voltage so as to bias the working electrode at a voltage less than about 0.15V and (b) measure a current corresponding to the concentration of the target analyte, wherein said electrical circuit has a communication module, wherein said communication module is configured to allow for two-way communication with a remote device, and wherein said electrochemical sensing system measuring current corresponding to the concentration of the target analyte multiple times during continued use once the working and reference electrode are inserted into said biofluid within said human or animal.

2. The electrochemical sensing system of claim 1, further comprising:

a biosensing molecule disposed on the working electrode and operative to catalytically decompose a non-electroactive target analyte to yield an electroactive by-product.

3. The electrochemical sensing system of claim 2, wherein the biosensing molecule is glucose oxidase.

4. The electrochemical sensing system of claim 1, further comprising:

a selectivity layer disposed on the working electrode, the selectivity layer configured to prevent interferents from diffusing to the surface of the working electrode.

5. The electrochemical sensing system of claim 4, wherein the interferents include at least one of an ascorbic acid, uric acid, and acetaminophen.

6. The electrochemical sensing system of claim 1, wherein the sensitivity of the electrochemical sensing system is higher than a sensitivity of an electrochemical sensing system that includes a Ag/AgCl reference electrode.

7. An electrochemical sensing system, comprising:

a working electrode, wherein the working electrode is platinum, wherein said working electrode comprises a porous membrane, said porous membrane configured to at least one of control the diffusion of the target analyte to the surface of the working electrode and prevent biofouling of the working electrode;

a synthetic redox-active receptor disposed on the working electrode and configured to move between different electronic states, the synthetic redox-active receptor further configured to change its reduction potential upon binding the target analyte such that the target analyte does not decompose;

a reference electrode, wherein the reference electrode is iridium;

a housing, wherein said housing is configured to house said working and said reference electrodes and to allow for insertion of said working and said reference electrodes into a biofluid within a human or animal for sensing, wherein said working electrode and reference electrodes are removable from said housing for replacement;

and an electrical circuit electronically coupled to the working electrode and the reference electrode, the electrical circuit configured to: (a) provide a constant bias voltage so as to bias the working electrode at a voltage in the range of about −0.6 V to about 0.15 V such that the working electrode donates an electron to the synthetic redox-active receptor and moves the synthetic redox-active receptor into a more reduced state and to reduce signal noise and fouling of said working electrode from interfering species present in said biofluid during continued use, and (b) measure a current corresponding to the concentration of the target analyte, wherein said electrical circuit has a communication module, wherein said communication module is configured to allow for two-way communication with a remote device and wherein said electrochemical sensing system measuring current corresponding to the concentration of the target analyte multiple times during continued use once the working and reference electrode are inserted into said biofluid within said human or animal.

8. The electrochemical sensing system of claim 7, wherein the synthetic redox-active receptor includes a viologen, a conjugated pyridinium or a boronic acid.

9. The electrochemical sensing system of claim 7, wherein the target analyte is glucose or lactate.

10. An electrochemical sensing system, comprising:

a working electrode, wherein the working electrode is iridium, wherein said working electrode comprises a porous membrane, said porous membrane configured to at least one of control the diffusion of the target analyte to the surface of the working electrode and prevent biofouling of the working electrode;

a reference electrode, wherein the reference electrode is iridium;

a housing, wherein said housing is configured to house said working and said reference electrodes and to allow for insertion of said working and said reference electrodes, through the use of a needle or penetration device, into a biofluid within a human or animal for sensing, wherein said working electrode and reference electrodes are removable from said housing for replacement;

and an electrical circuit electronically coupled to the working electrode and the reference electrode, the electrical circuit configured to: (a) provide a constant bias voltage so as to bias the working electrode at a voltage such that a target analyte or a by-product of said target analyte decomposes wherein the electrical circuit is configured to bias the working electrode at less than about 0.15V to reduce signal noise and fouling of said working electrode from interfering species present in said biofluid during continued use and (b) measure a current corresponding to the concentration of the target analyte, wherein said electrical circuit has a communication module, wherein said communication module is configured to allow for two-way communication with a remote device, and wherein said electrochemical sensing system measuring current corresponding to the concentration of the target analyte multiple times during continued use once the working and reference electrode are inserted into said biofluid within said human or animal.

11. The electrochemical sensing system of claim 10, further comprising:

a biosensing molecule disposed on the working electrode and operative to catalytically decompose a non-electroactive target analyte to yield an electroactive by-product.

12. The electrochemical sensing system of claim 11, wherein the biosensing molecule is glucose oxidase.

13. The electrochemical sensing system of claim 10, further comprising:

a selectivity layer disposed on the working electrode, the selectivity layer configured to prevent interferents from diffusing to the surface of the working electrode.

14. The electrochemical sensing system of claim 13, wherein the interferents include at least one of an ascorbic acid, uric acid, and acetaminophen.

15. The electrochemical sensing system of claim 10, wherein the sensitivity of the electrochemical sensing system is higher than a sensitivity of an electrochemical sensing system that includes a Ag/AgCl reference electrode.

16. An electrochemical sensing system, comprising:

a working electrode, wherein the working electrode is iridium, wherein said working electrode comprises a porous membrane, said porous membrane configured to at least one of control the diffusion of the target analyte to the surface of the working electrode and prevent biofouling of the working electrode;

a synthetic redox-active receptor disposed on the working electrode and configured to move between different electronic states, the synthetic redox-active receptor further configured to change its reduction potential upon binding the target analyte such that the target analyte does not decompose;

a reference electrode, wherein the reference electrode is iridium;

a housing, wherein said housing is configured to house said working and said reference electrodes and to allow for insertion of said working and said reference electrodes into a biofluid within a human or animal for sensing, wherein said working electrode and reference electrodes are removable from said housing for replacement;

and an electrical circuit electronically coupled to the working electrode and the reference electrode, the electrical circuit configured to: (a) provide a constant bias voltage so as to bias the working electrode at a voltage in the range of about −0.6 V to about 0.15 V such that the working electrode donates an electron to the synthetic redox-active receptor and moves the synthetic redox-active receptor into a more reduced state and to reduce signal noise and fouling of said working electrode from interfering species present in said biofluid during continued use, and (b) measure a current corresponding to the concentration of the target analyte, wherein said electrical circuit has a communication module, wherein said communication module is configured to allow for two-way communication with a remote device and wherein said electrochemical sensing system measuring current corresponding to the concentration of the target analyte multiple times during continued use once the working and reference electrode are inserted into said biofluid within said human or animal.

17. The electrochemical sensing system of claim 16, wherein the synthetic redox-active receptor includes a viologen, a conjugated pyridinium or a boronic acid.

18. The electrochemical sensing system of claim 16, wherein the target analyte is glucose or lactate.

* * * * *